United States Patent [19]

Prentiss

[11] Patent Number: 5,127,276
[45] Date of Patent: Jul. 7, 1992

[54] INSPECTION DRAIN PLUG

[76] Inventor: Paul H. Prentiss, 402 Randwick Rd., Dothan, Ala. 36301

[21] Appl. No.: 685,840

[22] Filed: Apr. 15, 1991

Related U.S. Application Data

[63] Continuation-in-part of Ser. No. 475,093, Apr. 30, 1990, abandoned.

[51] Int. Cl.[5] ............................................. G01N 1/10
[52] U.S. Cl. ................................. 73/863.86; 141/321
[58] Field of Search ........... 73/863.86, 863.85, 864.63, 73/864.65, 864.66; 138/90; 141/83, 320, 321, 322

[56] References Cited

U.S. PATENT DOCUMENTS

| | | | |
|---|---|---|---|
| 993,269 | 5/1911 | Mowers | 141/322 X |
| 1,792,464 | 2/1931 | Miller | 141/322 X |
| 3,198,016 | 8/1965 | Poorman | 73/863.86 |
| 3,869,391 | 3/1975 | Kramer | 137/614.21 X |
| 4,289,027 | 9/1981 | Gleaves et al. | 73/863.86 X |
| 4,437,487 | 3/1984 | Marmon | 251/149.6 X |
| 4,530,421 | 7/1985 | Balch | 251/149.6 X |
| 4,580,453 | 4/1986 | Taylor | 73/863.86 |
| 4,745,894 | 5/1988 | Laipply et al. | 251/149.1 X |
| 4,776,430 | 10/1988 | Rule | 137/539 |
| 4,877,218 | 10/1989 | Kasner | 251/239 X |

*Primary Examiner*—Tom Noland
*Attorney, Agent, or Firm*—Pettis & McDonald

[57] ABSTRACT

An inspection drain plug that is removably connected to an aperture in a fluid reservoir. The drain plug comprises an outer hollow body having an open first end and an open second end, the first end being removably connected in a fluid flow relationship to the aperture of the fluid reservoir. A valve mechanism is connected to the outer body, such that the valve mechanism may be selectively operated between an open and closed position, so that the first end of the outer body is closed when the valve is in the closed position. The drain plug also comprises a biasing mechanism, whereby the valve is biased toward the closed position. The first end of an inner hollow body, having an open first end and a closed second end, is removably inserted within the second end of the outer body. Upon insertion of the inner body within the outer body the closed second end of the inner body operatively engages the valve, thereby selectively moving the valve between the closed position and the open position.

9 Claims, 1 Drawing Sheet

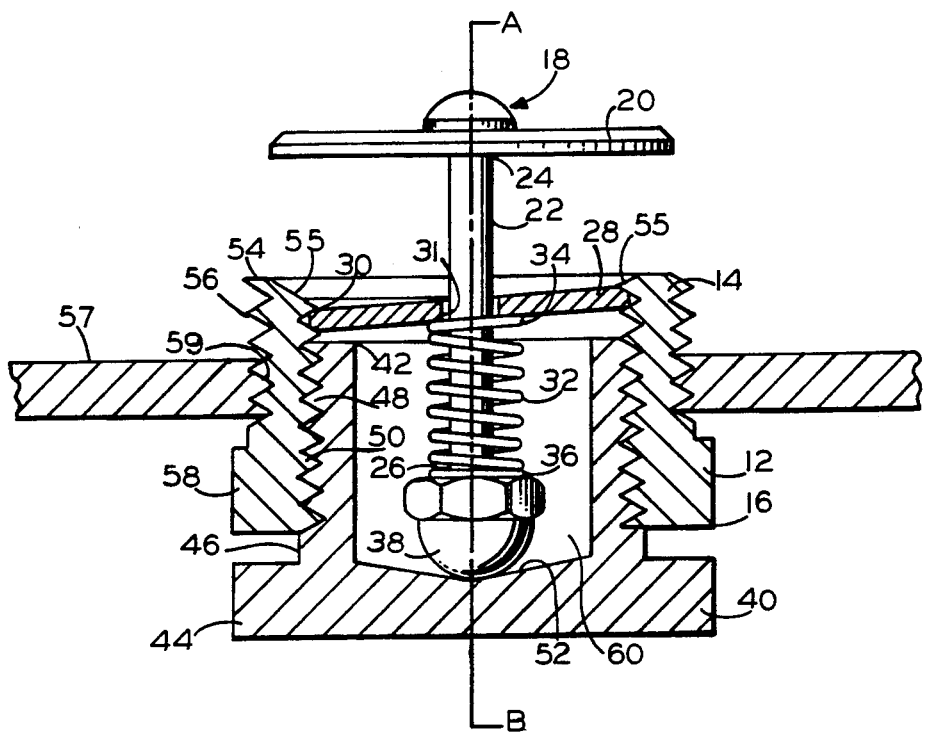
Fig_1_
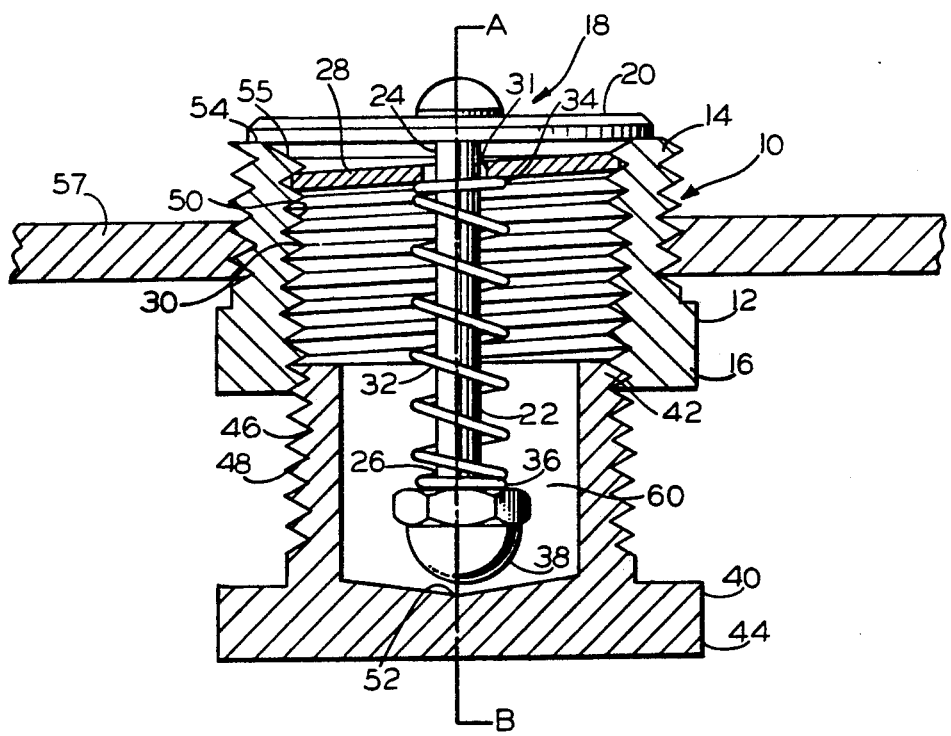
Fig_2_

INSPECTION DRAIN PLUG

RELATED APPLICATION

This application is a continuation-in-part of application Ser. No. 07/475,093, filed Apr. 30, 1990, entitled "Inspection Drain Plug" and filed in the name of Paul H. Prentiss and now abandoned.

BACKGROUND OF THE INVENTION

1. Field Of The Invention

The present invention relates to drain plugs for fluid reservoirs of the type used with equipment that contains a lubricant, coolant or other fluids, for example, transmissions, engines, axles or other gear boxes. More particularly, the inspection drain plug permits removal of small quantities of fluid for inspection purposes.

2. Description Of The Prior Art

At the present time, to inspect and analyze fluids contained within the reservoir of an apparatus, for example lubricants and coolants held within transmissions, engines, axles or other gear boxes, it is generally necessary to remove the drain plug from the bottom of the reservoir. Such removal then permits much of the fluid to drain out, making it necessary to replace it with a new fluid or replace the fluid that has been removed. In either case it is very expensive and time consuming.

There is a need for a means to remove a small amount of the fluid to inspect for contaminants that have collected in the bottom of the reservoir. Frequent inspection will determine when the fluid must be replaced and whether there is excessive wear within the parts of the equipment.

SUMMARY OF THE INVENTION

The present invention may be installed as a retrofit part, replacing an existing drain plug in a fluid reservoir, or may be installed as original equipment during the equipment manufacturing process. The present invention comprises an inner and outer body. The outer body is installed through the wall of the reservoir in fluid flow communication with the fluids stored therein. The hollow outer body has an open first end and an open second end. The first end is removably connected in a fluid flow relationship to the drain aperture in a fluid reservoir. A valve means is connected to the outer body by a support means so that the valve may be selectively operated between an open and a closed position, such that the first end of the outer body is closed when the valve is in the closed position. A biasing means biases the valve toward the closed position.

A hollow inner body has an open first end and a closed second end. The first end of the inner body is removably inserted into the second end of the outer body, such that the closed end operatively engages the valve means moving the valve means from the biased closed position to an open position.

In a preferred embodiment, the inner body can be removed, closing a valve on the outer body, thereby stopping the fluid from draining through the opening left by the removal of the inner body. A portion of the material is collected within the inner body and can be inspected and analyzed for contaminants. The inner body is then cleaned and replaced in a few minutes eliminating the need to drain most of the fluid just to obtain a small sample needed for inspection and testing of the fluid.

BRIEF DESCRIPTION OF THE DRAWING

For a fuller understanding of the nature and objects of the invention, reference should be had to the following detailed description taken in connection with the accompanying drawings, in which:

FIG. 1 is a cross-sectional view of a preferred embodiment of the inspection drain plug inserted in a fluid reservoir wall and illustrating the open position.

FIG. 2 is a cross-sectional view of a preferred embodiment of the inspection drain plug illustrating the closed position.

DETAILED DESCRIPTION

A preferred embodiment for the inspection drain plug of this invention is illustrated in drawing FIGS. 1 and 2 and is generally indicated as 10. Referring to the view of FIG. 1, it can be seen that the inspection drain plug 10, which is of generally cylindrical configuration and is generally symmetrical about axis A, is comprised of an outer hollow body 12 that has a first open end 14 and a second open end 16. Connected to the outer body 12 is a valve means, shown generally as 18. The valve means is comprised of a valve plate 20 and a valve stem 22, the valve stem 22 having a first end 24 and a second end 26. The first end 24 of the stem 22 is attached to the valve plate 20. The valve means 18 is connected to the outer body 12 by a support means. In the preferred embodiment, the support means is conveniently located proximal to the first end 14 of the outer body 12, and it may be comprised of a single support member 28 that is attached to opposing portions of the interior wall 30 of the outer body 12. In the preferred embodiment, the support member 28 is frictionally held within the threads 50 of the outer body 12; however, any suitable attaching means may be used. The support member 28 passes through the longitudinal axis A of the outer body 12 so that the center of the aperture 31 of the support member 28 resides generally on the axis A. The stem 22 of the valve 18 is slidably inserted in aperture 31.

A biasing means, suitably spring 32, has a first end 34 and a second end 36. Spring 32 is mounted upon the stem 22 such that the first end 34 of the spring 32 rests against the support member 28 and the second end 36 of the spring 32 is captured by a retaining means 38 that is located proximal to the second end 26 of the valve stem 22. The retaining means 38 may be any suitable construction, including, but not limited to, threaded nuts, the staking of a small plate to the valve stem 22 or a cotter pin passing through an aperture in the valve stem 22.

A hollow inner body 40 has an open first end 42 and a closed second end 44. The inner body 40 is sized and configured so that the open end 42 may be inserted into the open second end 16 of the outer body 12 and attached thereto. In the preferred embodiment as shown in FIG. 1 the attaching means is by threadable engagement. The inner body 40 has an exterior surface 46 and, upon a portion thereof, threads 48 have been formed. Threads 50 are formed upon at least a portion of the interior wall 30 of the outer body 12 so that the inner body 40 may be threadably engaged with the outer body 12. This is the preferred means for attachment, however, any suitable means, including, but not limited to, bayonet fasteners may be used.

The inner body 40 has an axis B that coincides with axis A of the valve stem. The closed end 44 of the inner body 40 has a depression 52 located upon its axis B, such that, when the inner body 40 engages the outer body 12, the depression 52 of the closed end 44 of the inner body 40 engages the retaining means 38 of the valve stem 22, operatively moving the valve plate 20 away from the first end 14 of the outer body 12. The retaining means 38 of the valve stem 22 is captured by the depression 52 to assist in maintaining the preferred axial alignment of the valve stem 22 with the axis B of the inner body 40. In the preferred embodiment the retaining means 38 comprises an acorn nut into which the valve stem 22 is inserted; however, in other embodiments the second end 26 of the valve stem 22 may engage the closed end 44 of the inner body 40.

When the inner body 40 is removed from the outer body 12 the spring 32 causes the valve means 18 to move to the closed position as seen in FIG. 2, so that the valve plate 20 engages peripheral edge 54 of the first end 14 of the outer body 12. The valve plate 20 is sized and configured to engage generally the entire peripheral edge 54, thereby closing the open first end 14 of the outer body 12. Therefore, by selectively inserting or removing the inner body 40 into the outer body 12 the valve means 18 is selectively moved between a closed position illustrated in FIG. 2, and an open position, illustrated in FIG. 1.

A portion of the exterior surface 58 of the outer body 12 that is proximal to the second end 16 may comprise a plurality of sides (not shown) to assist in gripping of the outer body 12 by a wrench. In the same fashion, a portion of the exterior surface 46 of the inner body 40 may comprise a plurality of sides (not shown) for gripping by a wrench.

A portion 55 of the peripheral edge 54 is sloped radially inwardly creating a wider open end 14 for the capture of contaminants. The inspection drain plug 10 may be made from any suitable material, including, but not limited to, steel or plastic.

Having thus set forth a preferred construction for the inspection drain plug 10 of this invention, it is to be remembered that this is but a preferred embodiment. Attention is now invited to a description of the use of the inspection drain plug 10. In the aftermarket, the inspection drain plug 10 is sized and configured to replace the standard drain plug that is removably connected to an aperture in the wall of a fluid reservoir 57, as shown in FIG. 1. As further shown in FIG. 1, the outer body 12 has threads 56 formed on a portion of the exterior surface 58 of the outer body 12 that are engageable with the threaded aperture 59 of a fluid reservoir 57. Any suitable connecting means may be provided on the outer body 12 that is compatible with a fastening means on the reservoir apertures. The standard plug (not shown) is removed and the assembled inspection drain plug 10 is inserted in its place. The fluid is then placed within the reservoir, a portion of which is shown as 57. Subsequently, the inner body 40 may be removed from the outer body 12 so that a sample of the fluid may be taken. As the inner body is removed, the valve means 18 is moved to the closed position by the spring 32 so that the valve plate 20 engages the peripheral edge 54 of the first end 14 of the outer body 12. The first end 14 of the outer body is now closed so that the fluid will generally not leak from the fluid reservoir 57. While the inspection drain plug 10 was inserted within the fluid reservoir 57, a portion of the fluid filled the hollow interior 60 of the inner body 40, and, in addition, the hollow interior 60 captured a portion of any contaminants, including any metallic particles that fall to the bottom of the reservoir 57. When the inner body 40 is removed, the captured fluid and contaminants are removed for inspection. After inspection the hollow interior 60 of the inner body 40 is cleaned and reinserted within the outer body 12. The depression 52 in the closed end 44 of the inner body 40 engages the second end 26 of the valve stem 22 slidably moving the first end 24 of the valve stem 22 and the valve plate 20 away from the peripheral edge 54 of the outer body 12, thereby moving the valve to the open position. In the open position, the inspection drain plug 10 may now receive a new sample of the fluid and any contaminants generated within the reservoir 57.

It will thus be seen that the objects set forth above, among those made apparent from the preceding description, are efficiently attained, and since certain changes may be made in the above article without departing from the scope of the invention, it is intended that all matter contained in the above description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. An inspection drain plug removably connected to an aperture in a fluid reservoir, said drain plug comprising
   an outer hollow body having an open, axial, first end and an open, axial, second end, said first end of said body being removably connected in fluid flow relation to the aperture in the fluid reservoir;
   valve means, connected to said outer body by a support means, said valve being selectively operated between an open position and a closed position, such that said first end of said outer body is closed when said valve is in said closed position;
   biasing means causing said valve to be biased toward said closed position; and
   an inner hollow body having an open first end and a closed second end, said first end of said inner body being removably inserted within said second end of said outer body, said closed end of said inner body operatively engaging said valve means, wherein removal or insertion of said inner body selectively and respectively moves said valve means between said closed position and said open position.

2. An inspection drain plug as in claim 1 wherein said valve means comprises a valve plate, and a valve stem having a first end and a second end, said first end being attached to said valve plate, said valve stem being supported for movement by said support means, said first end of said outer body further comprising a peripheral edge, said valve plate being sized and configured to engage said peripheral edge.

3. An inspection drain plug as in claim 2 wherein said biasing means comprises a spring having a first and a second end, said first end of said spring resting against said support means, said second end of said spring being connected to said second end of said valve stem such that when said inner body is inserted into said outer body, said closed end of said inner body engages said second end of said valve stem moving said second end of said valve stem toward said first end of said outer body and moving said valve to said open position whereby said spring is compressed against said support means.

4. An inspection drain plug as in claim 1 wherein said valve means further comprises
- a valve plate and a valve stem, said valve stem having a first end and a second end, said first end being attached to said valve plate
- a retaining means attached to said second end of said valve stem, said retaining means engaging said closed end of said inner body, and said support means comprises an aperture therethrough that slideably receives said valve stem.

5. An inspection drain plug as in claim 1 wherein said closed end of said inner body further comprises a depression that operatively engages said valve means.

6. An inspection drain plug as in claim 1 wherein
- said outer body further comprises an interior wall, and
- said support means comprises at least one member extending inwardly from said interior wall of said outer body, said member supporting said valve means for movement.

7. An inspection drain plug as in claim 1 wherein said outer body further comprises an exterior surface having threads formed thereon, whereby the outer body is threadably insertable within a threaded aperture in the fluid reservoir wall.

8. An inspection drain plug as in claim 1 wherein
- said outer body further comprises an interior wall, said interior wall having threads formed thereon, and
- said inner body further comprises an outer wall having threads formed thereon, said inner body being configured and dimensioned such that said inner body is threadably engageable with said outer body.

9. An inspection drain plug as in claim 1 wherein said first end of said outer body comprises a peripheral edge and said peripheral edge slopes radially inwardly toward said second end of said outer body.

* * * * *